(12) United States Patent
Czub et al.

(10) Patent No.: US 8,409,588 B2
(45) Date of Patent: Apr. 2, 2013

(54) RECOMBINANT FOOT AND MOUTH DISEASE VACCINE

(76) Inventors: Markus Czub, Masitoba (CA); Alfonso Clavijo, Manitoba (CA)

(*) Notice: Subject to any disclaimer, the term of this patent is extended or adjusted under 35 U.S.C. 154(b) by 904 days.

(21) Appl. No.: 11/721,451

(22) PCT Filed: Dec. 14, 2005

(86) PCT No.: PCT/CA2005/001893
§ 371 (c)(1),
(2), (4) Date: Feb. 23, 2011

(87) PCT Pub. No.: WO2006/063445
PCT Pub. Date: Jun. 22, 2006

(65) Prior Publication Data
US 2011/0287053 A1    Nov. 24, 2011

Related U.S. Application Data

(60) Provisional application No. 60/635,610, filed on Dec. 14, 2004, provisional application No. 60/643,579, filed on Jan. 14, 2005.

(51) Int. Cl.
*A61K 39/12* (2006.01)
*C12N 7/00* (2006.01)
*C12N 15/63* (2006.01)
*A61P 37/00* (2006.01)

(52) U.S. Cl. ............... 424/204.1; 435/320.1; 435/235.1

(58) Field of Classification Search ......................... None
See application file for complete search history.

(56) References Cited

U.S. PATENT DOCUMENTS
2004/0001864 A1    1/2004 King et al.

FOREIGN PATENT DOCUMENTS
WO    WO03083095    9/2003

OTHER PUBLICATIONS

Abrams et al. (Journal of General Virology. 1995; 76: 3089-3098).*
Grubman, M.J. and Baxt, B. Foot and mouth disease, Clinical Microbiology Reviews, 2004 vol. 7 No. 2 pp. 465-495.
Lewis, S.A. et al Expression, processing, and assembly of Foot and Mouth disease virus capsid structures in heterologous systems: Induction of a neutralizing antibody response in guinea pigs. Journal of Virology, 1991 vol. 65 No. 12 pp. 6572-6580.
Balamurugan, V. et al Protective immune response of the capsid precursor polypeptide (p1) of foot and mouth disease virus type "o" produced in Pichia pastoris. Virus Research 2003 vol. 92 pp. 141-149.

* cited by examiner

*Primary Examiner* — Shanon A Foley
(74) *Attorney, Agent, or Firm* — Michael R Williams; Ade & Company Inc

(57) ABSTRACT

A foot and mouth disease virus (FMDV) vaccine and method for producing same is described wherein the N terminal portion of the FMDV polyprotein, encoding the four structural proteins, 1A, 1B, 1C, and 1D, are each separated by a non-FMDV protease, preferably a cellular protease, for example, furin. The expression system may be transformed into a cell expressing the non-FMDV protease and the resulting particles recovered for use as a vaccine.

8 Claims, 4 Drawing Sheets

| | | |
|---|---|---|
| Capsid | 1 | gagqsspatgsqnqsgntgsiinnyymqqyqnsmdtqlgdnaisggsneg |
| Modified | 1 | gagqsspatgsqnqsgntgsiinnyymqqyqnsmdtqlgdnaisggsneg |
| Capsid | 51 | stdttsthttntqnndwfsklassafsglf[redacted]dkkteettlledril |
| Modified | 51 | stdttsthttntqnndwfsklassafsglf[redacted]dkkteettlledril |
| Capsid | 101 | ttrnghttsttqssvgvtygyataedfvsgpntsgletrvvqaerffkth |
| Modified | 101 | ttrnghttsttqssvgvtygyataedfvsgpntsgletrvvqaerffkth |
| Capsid | 151 | lfdwvtsdpfgrcyllelptdhkgvygsltdsyaymrngwdvevtavgnq |
| Modified | 151 | lfdwvtsdpfgrcyllelptdhkgvygsltdsyaymrngwdvevtavgnq |
| Capsid | 201 | fnggcllvamvpelcsidkrelyqltlfphqfinprtnmtahitvpfvgv |
| Modified | 201 | fnggcllvamvpelcsidkrelyqltlfphqfinprtnmtahitvpfvgv |
| Capsid | 251 | nrydqykvhkpwtlvvmvvapltvntegapqikvyaniaptnvhvage[redacted] |
| Modified | 251 | nrydqykvhkpwtlvvmvvapltvntegapqikvyaniaptnvhvage[redacted] |
| Capsid | 301 | [redacted]gifpvacsdgygglvttdpktadpaygkvfnppprnmlpgrftnfldv |
| Modified | 301 | [redacted]gifpvacsdgygglvttdpktadpaygkvfnppprnmlpgrftnfldv |
| Capsid | 351 | aeacptflhfeggvpyvttktdsdrvlaqfdlslaakhmsntflaglaqy |
| Modified | 351 | aeacptflhfeggvpyvttktdsdrvlaqfdlslaakhmsntflaglaqy |
| Capsid | 401 | ytqysgtinlhfmftgptdakarymiayappgmeppktpeaaahcihaew |
| Modified | 401 | ytqysgtinlhfmftgptdakarymiayappgmeppktpeaaahcihaew |
| Capsid | 451 | dtglnskftfsipylsaadyaytasdaaettnvqgwvclfqithgkadgd |
| Modified | 451 | dtglnskftfsipylsaadyaytasdaaettnvqgwvclfqithgkadgd |
| Capsid | 501 | alvvlasagkdfelrlpv[redacted]ttsagesadpvtatvenyggetqvqrr |
| Modified | 501 | alvvlasagkdfelrlpv[redacted]ttsagesadpvtatvenyggetqvqrr |
| Capsid | 551 | qhtdvsfildrfvkvtpkdqinvldlmqtpahtlvgallrtatyyfadle |
| Modified | 551 | qhtdvsfildrfvkvtpkdqinvldlmqtpahtlvgallrtatyyfadle |
| Capsid | 601 | vavkhegnltwvpngapetaldnttnptayhkapltrlalpytaphrvla |
| Modified | 601 | vavkhegnltwvpngapetaldnttnptayhkapltrlalpytaphrvla |
| Capsid | 651 | tvyngnckygespvtnvrgdlqvlaqkaartlptsfnygaikatrvtell |
| Modified | 651 | tvyngnckygespvtnvrgdlqvlaqkaartlptsfnygaikatrvtell |
| Capsid | 701 | yrmkraetycprpllaihpsearhkqkivapvkq |
| Modified | 701 | yrmkraetycprpllaihpsearhkqkivapvkq |

FIGURE 4

SEQUENCE LISTING

```
<160> NUMBER OF SEQ ID NOS: 1

<210> SEQ ID NO 1
<211> LENGTH: 734
<212> TYPE: PRT
<213> ORGANISM: artificial
<220> FEATURE:
<223> OTHER INFORMATION: genetically engineered fusion protein
```

```
<220> FEATURE:
<221> NAME/KEY: peptide
<222> LOCATION: (1)..(80)
<223> OTHER INFORMATION: FMDV protein 1A
<220> FEATURE:
<221> NAME/KEY: site
<222> LOCATION: (81)..(85)
<223> OTHER INFORMATION: furin cleavage site
<220> FEATURE:
<221> NAME/KEY: peptide
<222> LOCATION: (86)..(298)
<223> OTHER INFORMATION: FMDV protein 1B
<220> FEATURE:
<221> NAME/KEY: site
<222> LOCATION: (299)..(303)
<223> OTHER INFORMATION: furin cleavage site
<220> FEATURE:
<221> NAME/KEY: peptide
<222> LOCATION: (304)..(518)
<223> OTHER INFORMATION: fmdv protein 1C
<220> FEATURE:
<221> NAME/KEY: site
<222> LOCATION: (519)..(523)
<223> OTHER INFORMATION: furin cleavage site
<220> FEATURE:
<221> NAME/KEY: peptide
<222> LOCATION: (524)..(734)
<223> OTHER INFORMATION: fmdv protein 1D

<400> SEQUENCE: 1
```

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Arg Arg His Arg Arg Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Phe Val
        115                 120                 125

Ser Gly Pro Asn Thr Ser Gly Leu Glu Thr Arg Val Val Gln Ala Glu
    130                 135                 140

Arg Phe Phe Lys Thr His Leu Phe Asp Trp Val Thr Ser Asp Pro Phe
145                 150                 155                 160

Gly Arg Cys Tyr Leu Leu Glu Leu Pro Thr Asp His Lys Gly Val Tyr
                165                 170                 175

Gly Ser Leu Thr Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Leu Cys Ser Ile Asp Lys Arg Glu Leu Tyr Gln
    210                 215                 220

Leu Thr Leu Phe Pro His Gln Phe Ile Asn Pro Arg Thr Asn Met Thr
225                 230                 235                 240

Ala His Ile Thr Val Pro Phe Val Gly Val Asn Arg Tyr Asp Gln Tyr
                245                 250                 255

Lys Val His Lys Pro Trp Thr Leu Val Val Met Val Val Ala Pro Leu

-continued

```
                    260                 265                 270
Thr Val Asn Thr Glu Gly Ala Pro Gln Ile Lys Val Tyr Ala Asn Ile
            275                 280                 285
Ala Pro Thr Asn Val His Val Ala Gly Glu Arg Arg His Arg Arg Gly
            290                 295                 300
Ile Phe Pro Val Ala Cys Ser Asp Gly Tyr Gly Gly Leu Val Thr Thr
305                 310                 315                 320
Asp Pro Lys Thr Ala Asp Pro Ala Tyr Gly Lys Val Phe Asn Pro Pro
            325                 330                 335
Arg Asn Met Leu Pro Gly Arg Phe Thr Asn Phe Leu Asp Val Ala Glu
            340                 345                 350
Ala Cys Pro Thr Phe Leu His Phe Glu Gly Gly Val Pro Tyr Val Thr
            355                 360                 365
Thr Lys Thr Asp Ser Asp Arg Val Leu Ala Gln Phe Asp Leu Ser Leu
            370                 375                 380
Ala Ala Lys His Met Ser Asn Thr Phe Leu Ala Gly Leu Ala Gln Tyr
385                 390                 395                 400
Tyr Thr Gln Tyr Ser Gly Thr Ile Asn Leu His Phe Met Phe Thr Gly
                405                 410                 415
Pro Thr Asp Ala Lys Ala Arg Tyr Met Ile Ala Tyr Ala Pro Pro Gly
            420                 425                 430
Met Glu Pro Pro Lys Thr Pro Glu Ala Ala His Cys Ile His Ala
            435                 440                 445
Glu Trp Asp Thr Gly Leu Asn Ser Lys Phe Thr Phe Ser Ile Pro Tyr
            450                 455                 460
Leu Ser Ala Ala Asp Tyr Ala Tyr Thr Ala Ser Asp Ala Ala Glu Thr
465                 470                 475                 480
Thr Asn Val Gln Gly Trp Val Cys Leu Phe Gln Ile Thr His Gly Lys
                485                 490                 495
Ala Asp Gly Asp Ala Leu Val Val Leu Ala Ser Ala Gly Lys Asp Phe
            500                 505                 510
Glu Leu Arg Leu Pro Val Arg Arg His Arg Arg Thr Thr Ser Ala Gly
            515                 520                 525
Glu Ser Ala Asp Pro Val Thr Ala Thr Val Glu Asn Tyr Gly Gly Glu
            530                 535                 540
Thr Gln Val Gln Arg Arg Gln His Thr Asp Val Ser Phe Ile Leu Asp
545                 550                 555                 560
Arg Phe Val Lys Val Thr Pro Lys Asp Gln Ile Asn Val Leu Asp Leu
                565                 570                 575
Met Gln Thr Pro Ala His Thr Leu Val Gly Ala Leu Leu Arg Thr Ala
            580                 585                 590
Thr Tyr Tyr Phe Glu Asp Leu Glu Val Ala Val Lys His Glu Gly Asn
            595                 600                 605
Leu Thr Trp Val Pro Asn Gly Ala Pro Glu Thr Ala Leu Asp Asn Thr
            610                 615                 620
Thr Asn Pro Thr Ala Tyr His Lys Ala Pro Leu Thr Arg Leu Ala Leu
625                 630                 635                 640
Pro Tyr Thr Ala Pro His Arg Val Leu Ala Thr Val Tyr Asn Gly Asn
                645                 650                 655
Cys Lys Tyr Gly Glu Ser Pro Val Thr Asn Val Arg Gly Asp Leu Gln
            660                 665                 670
Val Leu Ala Gln Lys Ala Ala Arg Thr Leu Pro Thr Ser Phe Asn Tyr
            675                 680                 685
```

-continued

```
Gly Ala Ile Lys Ala Thr Arg Val Thr Glu Leu Leu Tyr Arg Met Lys
        690             695             700

Arg Ala Glu Thr Tyr Cys Pro Arg Pro Leu Leu Ala Ile His Pro Ser
705             710             715                         720

Glu Ala Arg His Lys Gln Lys Ile Val Ala Pro Val Lys Gln
                725             730
```

RECOMBINANT FOOT AND MOUTH DISEASE VACCINE

PRIOR APPLICATION INFORMATION

This application claims the benefit of U.S. Ser. No. 60/635,610, filed Dec. 14, 2004 and U.S. Ser. No. 60/643,579, filed Jan. 14, 2005.

BACKGROUND OF THE INVENTION

Foot-and-mouth disease (FMD) is a usually acute disease affecting cloven-hoofed domestic and wild animals like cattle, buffalo, sheep, deer, and pigs. The disease is associated with a high morbidity and low mortality. Subclinical and persistent infections occur and pose major problems for disease control. The virus is highly contagious and is transmitted by contact with infected animals and contaminated materials, humans, and non-susceptible animals. Over the past twenty years, FMD has been endemic in large areas of Asia, Africa, Southern America, and occasionally Europe, but not in Australia and Northern America. Disease control measures often included massive culling. This strategy has received intense criticism. Current vaccines for FMD are readily available and safe; however, due to the complex production process and other drawbacks they are not employed as a universal and global weapon against FMD.

Outbreaks of FMD result in devastating and drastic consequences for both animals and humans. Affected countries suffer from substantial loss in livestock and animal products, and in export markets, both short- and long-term. Additional costs, distress and suffering arise from eradication measurements, compensation policies, and disruption of normal living.

Vaccination against FMDV is an established and specific tool to help control both FMD eradication and outbreaks. Definitive strategies, however, do not exist and depend on a broad range of implications. There are no antiviral treatments for FMDV.

FMDV is an antigenically variable virus consisting of seven serotypes (European types A, O and C; African types SAT1, SAT2 and SAT3; and an Asiatic type Asia 1) and dozens of subtypes (see for example Kleid et al., 1981, Science 214: 1125-1129). Immunity to one serotype does not provide protection against the others and in some cases, immunity to one subtype will not protect against other members of the same subtype. Currently used vaccines consist of tissue culture grown virus, which for some preparations are partially purified and which are typically inactivated by binary ethyleneimine (BEI).

Modern FMD vaccines, in combination with other measures, can be used to contain and eradicate FMD outbreaks. Contact transmission of FMDV is rapidly reduced within 3-5 days after vaccination of pigs, cattle, sheep, and other animals.

However, some concerns exist over the use of FMD vaccines. After exposure to FMDV, vaccination may only prevent disease but not infection, and some animals may become persistently infected carriers of FMDV. Using approved diagnostic tests, it is difficult, if not impossible to differentiate vaccinated from infected or convalescent animals. Based on the current technology, production of vaccines requires handling of live virus in high containment facilities, which excludes countries such as the USA from vaccine production.

US Published Patent Application 2004/0001864 teaches a vaccine against foot-and-mouth disease wherein empty capsids are produced by coexpressing P1 and protease 3C.

U.S. Pat. No. 5,864,008 teaches a Th-cell epitope derived from VP3 capsid protein of FMDV.

U.S. Pat. No. 5,612,040 teaches a foot-and-mouth disease vaccine comprising deletion of the G-H loop of VP1 which results in an antigenic but non-infectious virus.

U.S. Pat. No. 5,824,316 teaches a genetically engineered foot-and-mouth disease virus wherein the leader proteinase has been deleted. The L proteinase-deleted viruses are able to assemble and grow in cells in culture, but are less toxic to infected cells within the cells, thereby producing an attenuated infection.

U.S. Pat. No. 6,048,538 teaches the use of immunodominant domains from FMDV non-structural proteins 3A, 3B and 3C and the use thereof for detecting anti-FMDV antibodies in animal body fluids.

Published US Patent Application 2003/0171314 teaches early protection of susceptible animals against FMDV by inoculating the animals with a vaccine comprising an interferon DNA sequence and optionally a foot-and-mouth disease vaccine.

U.S. Pat. No. 6,107,021 teaches a peptide composition comprising at least one target antigenic site derived from VP1 capsid protein of FMDV covalently linked to a helper T cell epitope.

Published PCT Application WO 03/083095 teaches insertion of a heterologous sequence between two furin cleavage sites within a carrier glycoprotein, such as the furin cleavage sites of an F protein of a Respiratory Syncytial Virus and using the resulting mutant virus as a multivalent vaccine.

Published US Patent Application 2004/0001864 teaches the preparation of empty FMDV capsids by expression of the P1 region and protease 3C. Mason et al. (Vaccines for OIE List A and Emerging Animal Diseases, 2003, Brown and Roth eds, Dev Biol Base1, Karger, vol 114: 79-88) teaches a similar method, involving the expression of a fragment of the P1 region and protease 3C for producing empty capsids.

Structures on the surface of the virus particle present antigenic sites that are important for the immune response to FMDV. In particular, fragments derived from surface peptide 1D elicit neutralizing antibodies that could protect animals from challenge. However, when used alone, 1D-based vaccines failed to induce sufficient immunity in challenge experiments. In general, the entire accessible surface of a virus would be expected to be antigenic and may thus assist in the generation of a strong immunity. Specific formulations of all, recombinantly expressed non-infectious FMDV capsid proteins appear to be as efficacious as a commercial vaccine, with regard to immunogenicity and resistance to challenge with FMDV.

SUMMARY OF THE INVENTION

According to a first aspect of the invention, there is provided an expression system comprising
a promoter operably linked to a nucleic acid molecule encoding a poly-protein, said polyprotein comprising:
FMDV 1A protein-nonFMDV protease recognition sequence-FMDV 1B protein-nonFMDV protease recognition sequence-FMDV 1C protein-nonFMDV protease recognition sequence-FMDV 1D protein.

According to a second aspect of the invention, there is provided a method of producing a foot and mouth disease virus-like particle comprising:
providing a host cell including an expression system comprising a promoter operably linked to a nucleic acid molecule encoding a poly-protein, said polyprotein comprising FMDV 1A protein-nonFMDV protease recognition sequence-FMDV 1B protein-nonFMDV protease recognition sequence-FMDV 1C protein-nonFMDV protease recognition sequence-FMDV 1D protein, said host cell expressing a protease recognizing said nonFMDV protease recognition sequence;

growing the host cell under conditions such that the polyprotein is produced, resolved into 1A, 1B, 1C and 1D by the protease and 1A, 1B, 1C and 1D assemble into virus-like particles; and recovering the virus-like particles.

According to a third aspect of the invention, there is provided the use of the virus-like particles prepared as described above as a vaccine.

BRIEF DESCRIPTION OF THE DRAWINGS

FIG. 2. Protein chart for the authentic and modified capsid polyproteins. Amino acid changes of the modified polyprotein are underlined in blue. These sites represent newly introduced furin cleavage sites.

FIG. 4. Blot showing cleavage of polypeptide by furin. Cells have been transfected with 3 different plasmids encoding for the original (left lane; "no cut") or modified (center and right lane) FMDV capsid (VP1-4). New cleavage sites (A, B, C) have been introduced as indicated (center and right lane) and utilized. The authentic A cleavage site is recognized by a cellular protease and partially cleaved (left lane). The modified FMDV capsids are cleaved to completion at B (center lane) and at A, B, and C (right lane). Since the blot is probed with a monoclonal antibody directed towards VP1 only proteins containing VP1 are visualised.

DESCRIPTION OF THE PREFERRED EMBODIMENTS

Figure 1:
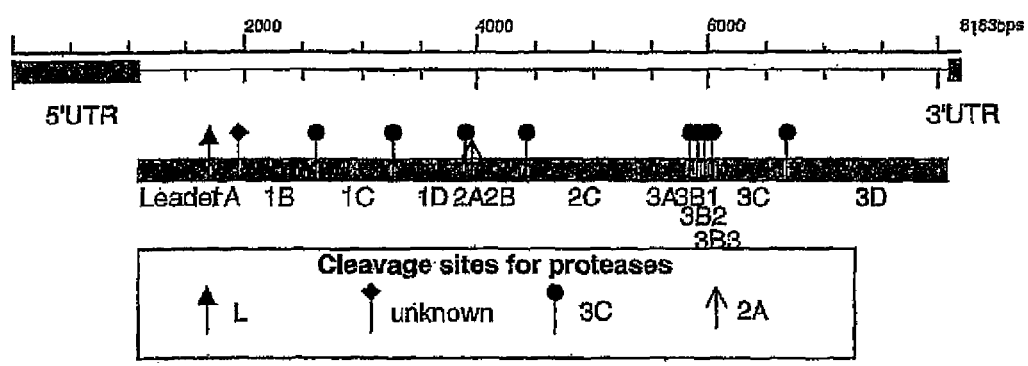
FIG. 1. Schematic diagram of the FMDV genome, strain 0, UKGJ3512001, and the open reading frame for the polyprotein. Protein cleavage sites and the respective proteases are indicated as arrows.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "cloven-hoofed" animal refers to domestic and wild animals, for example, but by no means limited to cattle, buffalo, sheep, deer, and pigs.

Non-infectious molecular approaches should preferably offer a safe production of vaccines, a platform based technology for all viral strains, and the inclusion of a marker for distinguishing between vaccinated and non-vaccinated animals. That is, one needs to be able to distinguish between vaccinated and infected animals. In one embodiment, as discussed herein, a vaccine or expression system that includes only FMDV capsid and not the FMDV polymerase proteins is used so that vaccinated animals (which will not have anti-polymerase antibodies but will have anti-capsid antibodies) and infected animals (which will have both anti-polymerase antibodies and anti-capsid antibodies) can be distinguished. In an alternative embodiment, the expression system or vaccine includes a marker gene. As will be appreciated by one of skill in the art, when expressed, the marker gene will produce a detectable marker, for example, an immune response to the product of the marker gene. Other suitable markers known in the art may also be used.

FMDV contains a single-stranded positive sense ribonucleic acid (RNA) genome of approximately 8,300 bases surrounded by an icosahedral capsid composed of 60 copies each of four structural proteins, 1A, 1B, 1C, and 1D. The RNA genome is translated as a single, long open-reading frame and codes for the four structural proteins and a number of non-structural proteins, which function in various aspects of the virus cycle. The viral polyprotein is co-translationally processed by at least three viral encoded proteinases ($L^{pro}$, 2A oligopeptide and $3C^{pro}$). Most of the cleavages are catalysed by $3CP^{pro}$ or a $3C^{pro}$-containing precursor, including the processing of the capsid precursor polypeptide, P1, into 1AB, 1C, and 1D. One exception is the maturation cleavage of the precursor capsid protein 1AB in the provirion to generate the capsid proteins 1A and 1B that occurs by an unknown mechanism. Only 1D, 1B, and 1C have been shown to be surface-exposed and an immunologically important loop found between the G and H beta strands of 1D has been identified as a prominent surface structure on the viral capsid. Cleavage of the polyprotein is essential and sufficient for virus particle formation.

Described herein is an FMDV vaccine and method for producing same wherein the N-terminal portion of the FMDV polyprotein, encoding the four structural proteins, 1A, 1B, 1C, and 1D, are expressed from an mRNA having at least a 5' cap and a 3' poly-A tail, transcribed from a newly manufactured cDNA. As will be appreciated by one of skill in the art, other modifications to the mRNA and/or cDNA may also be made, for example, sequence modifications including but by no means limited to those discussed below and structural modifications known in the art. The protein cleavage recognition sites at either ends of the proteins are modified and are accessible for a non-FMDV protease, preferably a cellular protease, for example, Furin. As will be appreciated by one of skill in the art, the protease cleavage sites are found at the junctions between 1A and 1B, between 1B and 1C and between 1C and 1D. As such, in most embodiments, the 5' end of 1A and the 3' end of 1D will not be modified.

As used herein, 1A, 1B, 1C and 1D refer to the amino acid sequences (and nucleotide sequences derived therefrom) of these proteins known in the art as discussed herein. Specifically, as shown in Table 1, sequences for a number of FMDV isolates are known and as discussed below sequences from these isolates can be used in the invention.

The consensus sequence for furin is Arg-X-Lys/Arg-Arg↓-, (Molloy et al., 1999, Trends in Cell Biology 9: 28-35).

As will be appreciated by one of skill in the art, other suitable cellular proteases may be used. Preferably, the protease cleavage site is approximately the same length and has a similar hydrophobicity and/or three dimensional structure and/or charge distribution as the native FMDV protease cleavage site.

Thus, in one embodiment of the invention, there is provided an expression system comprising a nucleic acid molecule encoding a polypeptide comprising 1A, 1B, 1C and 1D of FMDV each separated by a non-native FMDV protease cleavage site. In a preferred embodiment of the invention, the expression system comprises a suitable promoter operably linked to a nucleic acid encoding a polypeptide comprising 1A-non-FMDV PCS-1B-non-FMDV-PCS-1C-non-FMDV-PCS-1D, wherein "PCS" refers to "protease cleavage site". In a yet further embodiment, the nucleic acid encodes a polyprotein comprising 1A-furin PCS-1B-furin PCS-1C-furin PCS-1D.

Figure 4:
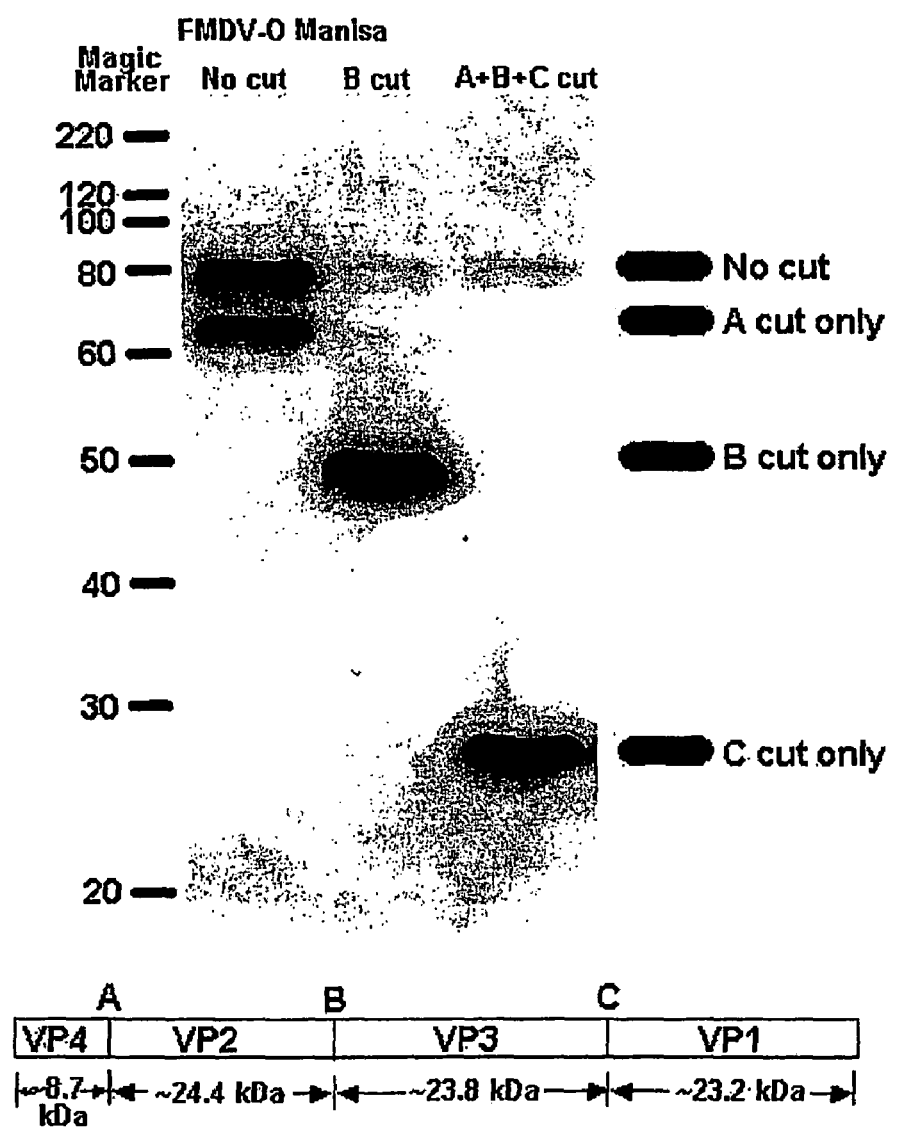

An example of such a construct is shown in FIG. 2 and in SEQ ID No. 1. As shown in FIG. 4, this construct was cleaved by furin into 1A, 1B, 1C and 1D proteins and assembled into virus-like particles. As will be apparent to one of skill in the art on examination of the sequence shown in FIG. 2 and SEQ ID No. 1, the FMDV strain is 0 Manisa. A similar construct was constructed using 1A, 1B, 1C and 1D proteins from A24 Cruzeiro also with furin sites engineered between the proteins and similar results were obtained, clearly indicating that the invention can be used to produce virus-like particles from different FMDV strains, as discussed below.

In another embodiment of the invention, there is provided a nucleic acid molecule encoding a polypeptide having a first domain that has at least 80% homology or at least 85% homology or at least 90% homology or at least 95% homology to amino acids 1-80 of SEQ ID No. 1, a second domain adjacent to the first domain that is a non-FMDV protease cleavage site; a third domain that has at least 80% homology or at least 85% homology or at least 90% homology or at least 95% homology to amino acids 86-298 of SEQ ID No. 1; a fourth domain that is a non-FMDV protease cleavage site; a fifth domain that has at least 80% homology or at least 85% homology or at least 90% homology or at least 95% homology to amino acids 304-518 of SEQ ID No. 1; a sixth domain that is a non-FMDV protease cleavage site; and a seventh domain that has at least 80% homology or at least 85% homology or at least 90% homology or at least 95% homology to amino acids 524-733 of SEQ ID No. 1. In a preferred embodiment, the non-FMDV protease cleavage site is a furin cleavage site as described above.

In another embodiment, there is provided a nucleic acid molecule having at least 80% homology or at least 85% homology or at least 90% homology or at least 95% homology to SEQ ID No. 1 and wherein the sequence of the furin cleavage sites (amino acids 81-85, 299-303 and 519-523 of SEQ ID No. 1) are such that the cleavage sites are recognized by furin, that is, are within the furin consensus sequence described above and are therefore functional for cleavage by furin.

In some embodiments, the expression system further includes a signal sequence for translocating the protein into the ER/golgi apparatus of the host cells.

Examples of suitable promoters include but are by no means limited to CMV-driven and baculovirus-driven promoters and vectors. As will be appreciated by one of skill in the art, any suitable promoter active in a cell line expressing the non-FMDV protease of choice may be used, although clearly, the stronger or more efficient the promoter, the higher the yield of particles.

As will be appreciated by one of skill in the art, any suitable cell line or cell type may be transfected or transformed with the expression system described herein. For example, in those embodiments wherein the non-FMDV protease is furin, any cell expressing the furin protease may be used. It is of note that the expression system may be expressed from a transient genetic element such as a plasmid or linear DNA or may be integrated into the genome of the host cell.

As will be appreciated by one of skill in the art, the cell or cell line of choice must also express the non-FMDV protease of choice. It is of note that the cell or cell line may express the protease naturally or as the result of genetic manipulation.

Examples of suitable cell lines include but are by no means limited to BHK and 293T.

Specifically, the expression system is transformed or transfected as discussed above and the cells are grown under conditions suitable for expression from the expression system. A poly-protein is produced which is cleaved by the non-FMDV protease, thereby resolving the poly-protein into 1A, 1B, 1C and 1D which in turn assemble into a particle. In some embodiments, the particles are secreted from the cell and can be recovered using means known in the art. In other embodiments, the particles are recovered using other suitable means known in the art.

As discussed herein, the particles can be used as a vaccine for vaccinating animals at risk of developing or contracting foot and mouth disease. It is of note that as discussed herein, the particles are non-replicative and can safely be used as a vaccine that accurately mimics the structure of native FMDV.

Thus, the cellular protease replaces the viral proteases $L^{pro}$, 2A oligopeptide and $3C^{pro}$ and an unknown protease. As a result of this arrangement, non-infectious eukaryotic and prokaryotic expression systems can be used to produce empty particles for use as a vaccine. Alternatively, the particles can also be used as diagnostic tools and/or to study old or new substances/drugs/mechanisms for potential antiviral activity against FMDV.

Referring to FIG. 2 and to SEQ ID No. 1, 1A corresponds to amino acids 1 to 80; 1B corresponds to amino acids 86 to 288; 1C corresponds to amino acids 304 to 518; and 1D corresponds to amino acids 524 to 734. As will be appreciated by one of skill in the art, these designations are relative and may vary between different serotypes and sub-types. Furthermore, the specific sequences of 1A, 1B, 1C and 1D are variable amongst serotypes and sub-types, several of which are documented and well known in the art (see for example, GenBank database accession numbers X00429 (A10), X00871(O1K), AJ251476 (A24) and AJ133357 (C Spain Olot) as well as Table 1).

Thus, in one embodiment of the invention, there is provided an expression system which expresses a fusion comprising 1A, 1B, 1C and 1D, each separated by a protease cleavage site. As will be appreciated by one of skill in the art, the specific amino acid sequence used for 1A, 1B, 1C and/or 1D may all be of any of the serotypes or subtypes of FMDV. In other embodiments, a multivalent vaccine may be generated for example by using 1A from one serotype or subtype fused to 1B and/or 1C and/or 1D from a different serotype or subtype.

Any suitable adjuvant known in the art may be used in combination with the vaccine. Examples of suitable adjuvants include but are by no means limited to alum, an acrylic or methacrylic acid polymer, or a water-in-oil or oil-in-water emulsion.

In some embodiments, disulphide bridges are added to increase the stability of the empty capsids using means known in the art.

In one embodiment of the invention, a cDNA molecule is generated by RT-PCR amplification of the 5' end of the FMDV genome, for example, strain 0, although any suitable FMDV could be used, including an unknown serotype or subtype implicated in an outbreak. Specifically, the primers are designed such that the resulting cDNA sequence will include the ORFs for 1A, 1B, 1C, and 1D. The cDNA is then subcloned into an appropriate expression vector. In some embodiments, the expression vector may be arranged such that the inserted cDNA includes for example an addition of an initial methionine, a stop codon and a poly-A tail.

The cDNA is then mutated to introduce cellular protease recognition sites, for example, furin cleavage sites between 1A-1B, 1B-1C, and 1C-1D. The expression vector is then transformed or transfected into a suitable host which is grown under conditions promoting expression of the cDNA, which in turn results in the production of empty FMDV capsid particles which are then recovered and used in the preparation of a vaccine.

In an alternative embodiment, the FMDV responsible for the outbreak is cloned or amplified by RT-PCR as discussed above and is sequenced. A cDNA template comprising 1A-PCS-1B-PCS-1C-PCS-1D wherein the 1A, 1B, 1C and 1D sequences are either derived from consensus sequences or from a specific FMDV isolate, for example, a common FMDV isolate is then mutated or otherwise modified so as to substantially correspond or correspond verbatim with the 1A, 1B, 1C and/or 1D sequence of the FMDV responsible for the outbreak. It is of note that a bank of template cDNAs as described above could be generated and the one with the greatest sequence homology to the FMDV responsible for the outbreak selected for mutation or modification.

Figure 3:
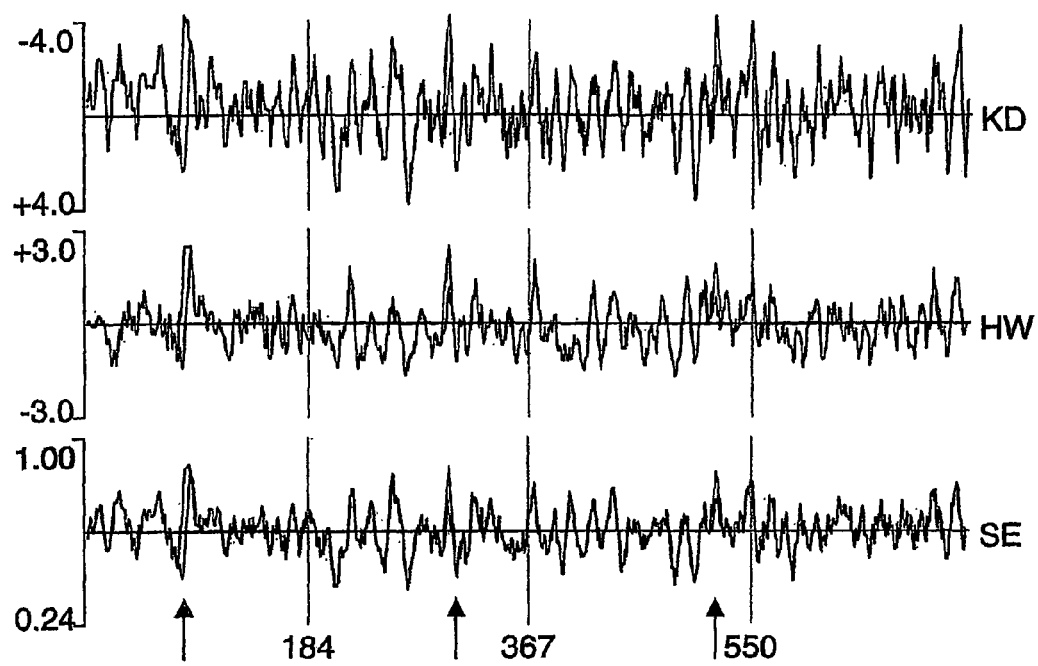
FIG. 3. Hydrophilicity of FMDV capsid proteins.

As shown in FIG. 3, FMDV proteins were translated from DNA and analyzed for hydrophilicity. The capsid polyprotein for FMDV, strain 0, is shown in black, and the modified capsid in red. Red arrows indicate newly introduced furin cleavage site. Predictions are calculated using methods derived from Kyte & Doolittle (KD) and Hopp & Woods (HW), and for surface exposure (SE). The analysis results are shown in a table format of numerical values and as a set of line graphs. For each amino acid residue, numerical values are given for KD, HW, and SE analyses. All three methods provide an indication of the hydrophilic character of the environment, and the range for each analysis is shown at the top of the column. Three line graphs plot the values calculated for each of the three analyses. For all three graphs, values above the axis line are hydrophilic or predicted to be exposed at the surface of the protein. KD values fall within a range of +4 to −4, with hydrophilic residues having a negative score. The most hydrophilic reside has a value of −4.5 (arginine). On the graphic display, values above the axis line are hydrophilic; values below the axis line are hydrophobic. KD represents a composite hydrophobicity scale derived from interpretation of free energy changes on a water-vapor phase transition and an analysis of buried side chains. Each value is the average of the values of 5 adjacent residues and is plotted at the middle residue. The range of values is approximately ±4 relative units. HW values fall within a range of −3 to +3, with hydrophilic residues having a positive score. The most hydrophilic residues have a value of ±3.0. On the graphic display, values above the axis line are hydrophilic; values below the axis line are hydrophobic. HW derived hydrophilicity values from a study of antigenicity and adjusted the values to maximize the accuracy of predicting antigenic determinants. Each value is the average of the values of 6 adjacent residues and is plotted at the middle point. The range of values is approximately ±3 relative units. The SE value is presented as a proportion of the residue, which is exposed on the surface of the protein. These values fall within a range of 0 to 1.000. The most exposed amino acid has a value of 0.97 (lysine). On the graphic display, peak values, which fall above the axis line, are predicted to be exposed on the surface of the protein. SE analysis uses the data of Janin, et al., which provides values representing the fraction of residues of a given amino acid that have a surface area of greater than 20 angstroms squared. High values therefore represent amino acids that are likely to be exposed on the surface of the protein. Plotted values are the average of 6 residues and are plotted at the middle point. Based on these predictions, the three-dimensional structure, the stability, and the immunogenicity of the modified capsid protein are expected to be very similar to the authentic FMDV, strain 0, capsid protein.

As will be appreciated by one of skill in the art, the native FMDV protease is of viral origin and would need to be co-expressed with the expression system expressing the capsid. This approach is inefficient due to the requirement for co-expression of both capsid proteins and protease in a single cell and would result in lower yield.

While the preferred embodiments of the invention have been described above, it will be recognized and understood that various modifications may be made therein, and the appended claims are intended to cover all such modifications which may fall within the spirit and scope of the invention.

Table 1 Exemplary FMDV Sequences

Foot-and-mouth disease virus A isolate a12valle 119 iso20, complete genome gi|46810760|gb| AY593752.1| [46810760]

Foot-and-mouth disease virus A isolate a13brazil iso75, complete genome gi|46810762|gb| AY593753.1|[46810762]

Foot-and-mouth disease virus A isolate a14 spain iso39, complete genome gi|46810764|gb| AY593754.1|[46810764]

Foot-and-mouth disease virus A isolate a15thailand iso43, complete genome gi|46810766|gb| AY593755.1| [46810766]

Foot-and-mouth disease virus A isolate a16belem iso80, complete genome gi|46810768|gb| AY593756.1| [46810768]

Foot-and-mouth disease virus A isolate a17 Aguarulbos iso83, complete genome gi|46810770|gb| AY593757.1| [46810770]

Foot-and-mouth disease virus A isolate a18 zulia iso40, complete genome gi|46810772|gb| AY593758.1|[46810772]

Foot-and-mouth disease virus A isolate a1b AYern iso41, complete genome gi|46810774|gb| AY593759.1| [46810774]

Foot-and-mouth disease virus A isolate a20ussr iso10, complete genome gi|46810776|gb| AY593760.1|[46810776]

Foot-and-mouth disease virus A isolate a21kenya iso77, complete genome gi|46810778|gb| AY593761.1|[46810778]

Foot-and-mouth disease virus A isolate a22iraq-95 iso95, complete genome gi|46810780|gb| AY593762.1| [46810780]

Foot-and-mouth disease virus A isolate a22iraq64 iso86, complete genome gi|46810782|gb| AY593763.1| [46810782]

Foot-and-mouth disease virus A isolate a22iraq70 iso92, complete genome gi|46810784|gb| AY593764.1| [46810784]

Foot-and-mouth disease virus A isolate a22turkey iso66, complete genome gi|46810786|gb| AY593765.1| [46810786]

Foot-and-mouth disease virus A isolate a23kenya iso8, complete genome gi|46810788|gb| AY593766.1|[46810788]

Foot-and-mouth disease virus A isolate a24 argentina iso9, complete genome gi|46810790|gb| AY593767.1| [46810790]

Foot-and-mouth disease virus A isolate a24cruzeiro iso71, complete genome gi|46810792|gb| AY593768.1| [46810792]

Foot-and-mouth disease virus A isolate a25 argentina iso38, complete genome gi|46810794|gb| AY593769.1| [46810794]

Foot-and-mouth disease virus A isolate a26arg iso74, complete genome gi|46810796|gb| AY593770.1|[46810796]

Foot-and-mouth disease virus A isolate a27columbia iso78, complete genome gi|46810798|gb| AY593771.1| [46810798]

Foot-and-mouth disease virus O strain Akesu/58, complete genome gi|21239433|gb| AF511039.1|[21239433]

Foot-and-mouth disease virus O strain China/1/99(Tibet), complete genome gi|21542501|gb|AF506822.21 [21542501]

Foot-and-mouth disease virus O, strain TAW/2/99 TC, complete genome gi|30145772|emb|AJ539136.1|FOO539136 [30145772]

Foot-and-mouth disease virus O, strain TAW/2/99 BOV, complete genome gi|30145774|emb|AJ539137.1|FOO539137 [30145774]

Foot-and-mouth disease virus O, strain Tibet/CHA/99, complete genome gi|30145776|emb|AJ539138.1|FOO539138 [30145776]

Foot-and-mouth disease virus O, strain SKR/2000, complete genome gi|30145778|emb|AJ539139.1|FOO539139 [30145778]

Foot-and-mouth disease virus O, strain SAR/19/2000, complete genome gi|30145780|emb|AJ539140.1|FOO539140 [30145780]

Foot-and-mouth disease virus O, strain UKG/35/2001, complete genome gi|30145782|emb|AJ539141.1|FOO539141 [30145782]

Foot-and-mouth disease virus HKN/2002, complete genome gi|33348772|gb| AY317098.1|[33348772]

Foot-and-mouth disease virus O strain OMIII, complete genome gi|33943915|gb|AY359854.1|[33943915]

Foot-and-mouth disease virus O isolate O/NY00, complete genome gi|37575129|gb| AY333431.1|[37575129]
Foot-and-mouth disease virus polyprotein gene, genomic RNA, serotype O, isolate FRA/1/2001, complete genome gi|45725010|emb|AJ633821.1|[45725010]
Foot-and-mouth disease virus O isolate o10phil54 iso54, complete genome gi|46810878|gb| AY593811.1| [46810878]
Foot-and-mouth disease virus O isolate o10phil76 iso76, complete genome gi|46810880|gb| AY593812.1| [46810880]
Foot-and-mouth disease virus O isolate o11Indonesia iso52, complete genome gi|46810882|gb| AY593813.1| [46810882]
Foot-and-mouth disease virus O isolate o1argentina iso5, complete genome gi|46810884|gb| AY593814.1| [46810884]
Foot-and-mouth disease virus O isolate o1bfs iso18, complete genome gi|46810886|gb| AY593815.1|[46810886]
Foot-and-mouth disease virus O isolate o1bfs46 iso46, complete genome gi|46810888|gb| AY593816.1|[46810888]
Foot-and-mouth disease virus O isolate o1brugge iso79, complete genome gi|46810890|gb| AY593817.1|[46810890]
Foot-and-mouth disease virus O isolate o1campos iso96, complete genome gi|46810892|gb| AY593818.1| [46810892]
Foot-and-mouth disease virus (FMDV) strain C, isolate c-s8c1, genomic RNA gi|6318187|emb|AJ133357.1|FDI133357[6318187]
Foot-and-mouth disease virus (FMDV) strain C, isolate rp99, genomic RNA gi|6318189|emb|AJ133358.11FAN133358 [6318189]
Foot-and-mouth disease virus (FMDV) strain C, isolate rp146, genomic RNA gi|6318191|emb|AJ133359.11FAN133359[6318191]
Foot-and-mouth disease virus C1 isolate c1noville iso56, complete genome gi|46810864|gb| AY593804.1| [46810864]
Foot-and-mouth disease virus C1 isolate c1ober iso88, complete genome gi|46810866|gb| AY593805.1|[46810866]
Foot-and-mouth disease virus C3 isolate c3ind iso19, complete genome gi|46810868|gb| AY593806.1|[46810868]
Foot-and-mouth disease virus C3 isolate c3resende iso1, complete genome gi|46810870|gb| AY593807.1| [46810870]
Foot-and-mouth disease virus C4 isolate C4 Tierra del Fuego iso2, complete genome gi|46810872|gb| AY593808.1| [46810872]
Foot-and-mouth disease virus C5 isolate c5arg iso60, complete genome gi|46810874|gb| AY593809.1|[46810874]
Foot-and-mouth disease virus C isolate cwald iso32, complete genome gi|46810876|gb| AY593810.1|[46810876]
Foot-and-mouth disease virus Asia1 strain YNBS/58, complete genome gi|37223495|gb| AY390432.1|[37223495]
Foot-and-mouth disease virus Asia 1 isolate asia1-1pak iso3, complete genome gi|46810846|gb| AY593795.1| [46810846]
Foot-and-mouth disease virus Asia 1 isolate asia1-2isrl3-63 iso6, complete genome gi|46810848|gb| AY593796.1| [46810848]
Foot-and-mouth disease virus Asia 1 isolate asia1-3kimron iso61, complete genome gi|46810850|gb| AY593797.1| [46810850]
Foot-and-mouth disease virus Asia 1 isolate asia1leb-89 iso89, complete genome gi|46810852|gb| AY593798.1| [46810852]
Foot-and-mouth disease virus Asia 1 isolate asia1leb4 iso4, complete genome gi|46810854|gb| AY593799.1| [46810854]
Foot-and-mouth disease virus Asia 1 isolate asia1leb83 iso28, complete genome gi|46810856|gb| AY593800.1| [46810856]
Foot-and-mouth disease virus Asia 1 isolate IND 321/01, complete genome gi|51340579|gb| AY687333.1| [51340579]
Foot-and-mouth disease virus Asia 1 strain IND 491/97, complete genome gi|51340581|gb| AY687334.1|[51340581]
Foot-and-mouth disease virus SAT 1 isolate sat1-20 iso11, complete genome gi|46810934|gb| AY593839.1| [46810934]
Foot-and-mouth disease virus SAT 1 isolate sat1-3swa iso14, complete genome gi|46810936|gb| AY593840.1| [46810936]
Foot-and-mouth disease virus SAT 1 isolate sat1-4srhod iso24, complete genome gi|46810938|gb| AY593841.1| [46810938]
Foot-and-mouth disease virus SAT 1 isolate sat1-5sa iso13, complete genome gi|46810940|gb| AY593842.1| [46810940]
Foot-and-mouth disease virus SAT 1 isolate sat1-6swa iso16, complete genome gi|46810942|gb| AY593843.1| [46810942]
Foot-and-mouth disease virus SAT 1 isolate sat1-7isrl iso12, complete genome gi|46810944|gb| AY593844.1| [46810944]
Foot-and-mouth disease virus SAT 1 isolate sat1bot iso47, complete genome gi|46810946|gb|AY593845.1| [46810946]
Foot-and-mouth disease virus SAT 1 isolate sat1rhod iso33, complete genome gi|46810948|gb| AY593846.1| [46810948]
Foot-and-mouth disease virus SAT2 genomic RNA for L, VP4, VP2, VP3, VP1, 2A, 2B, 2C, 3A, VPg1, VPg2, VPg3, pro coding polpolyprotein, strain KEN/3/57 gi|6572136|emb|AJ251473.1|FDI251473[6572136]
Foot-and-mouth disease virus SAT 2 clone ZIM/7/83, complete genome gi|33332022|gb| AF540910.1|[33332022]
Foot-and-mouth disease virus SAT 2 isolate sat2-1 rhod iso26, complete genome gi|46810950|gb| AY593847.1| [46810950]
Foot-and-mouth disease virus SAT 2 isolate sat2-2 iso25, complete genome gi|46810952|gb| AY593848.1| [46810952]

The invention claimed is:

1. An expression system comprising
a promoter operably linked to a nucleic acid molecule encoding a poly-protein, said polyprotein comprising:
FMDV 1A protein furin protease recognition sequence-FMDV 1B protein furin protease recognition sequence-FMDV 1C protein furin protease recognition sequence-FMDV 1D protein, wherein the poly-protein lacks FMDV proteinasse 2A.

2. The expression system according to claim 1 wherein the poly-protein has at least 85% homology to the polypeptide as set forth in SEQ ID NO:1.

3. The expression system according to claim 1 wherein the poly-protein has at least 90% homology to the polypeptide as set forth in SEQ ID NO:1.

4. The expression system according to claim 1 wherein the poly-protein has at least 95% homology to the polypeptide as set forth in SEQ ID NO:1.

5. A method of producing a foot and mouth disease virus-like particle comprising:
providing a host cell including an expression system comprising a promoter operably linked to a nucleic acid molecule encoding a poly-protein, said polyprotein comprising FMDV 1A protein furin protease recognition sequence-FMDV 1B protein furin protease recognition sequence-FMDV 1C protein furin protease recognition sequence-FMDV 1D protein, said host cell expressing furin protease;
growing the host cell under conditions such that the poly-protein is produced, resolved into 1A, 1B, 1C and 1D by the furin protease and 1A, 1B, 1C and 1D assemble into virus-like particles; and
recovering the virus-like particles.

6. The method according to claim 5 wherein the poly-protein has at least 85% homology to polypeptide as set forth in SEQ ID NO:1.

7. The method according to claim 5 wherein the poly-protein has at least 90% homology to polypeptide as set forth in SEQ ID NO:1.

8. The method according to claim 5 wherein the poly-protein has at least 95% homology to polypeptide as set forth in SEQ ID NO:1.

* * * * *